United States Patent [19]
Jordan et al.

[11] Patent Number: 5,772,432
[45] Date of Patent: Jun. 30, 1998

[54] DENTAL IMPRESSION TRAY WITH IMPROVED ADHESION TO IMPRESSION MATERIAL

[75] Inventors: Russell A. Jordan, Rancho Cucamonga; James F. Forbes, Monrovia, both of Calif.

[73] Assignee: Minnesota Mining & Manufacturing Co., St. Paul, Minn.

[21] Appl. No.: 733,588

[22] Filed: Oct. 18, 1996

[51] Int. Cl.$^6$ .................................................. A61C 9/00
[52] U.S. Cl. ................................................ 433/37; 433/47
[58] Field of Search ................................ 433/37, 41, 42, 433/43, 45, 46, 47, 48, 214

[56] References Cited

U.S. PATENT DOCUMENTS

| | | | |
|---|---|---|---|
| 4,251,209 | 2/1981 | Bekey et al. | 433/34 |
| 4,445,854 | 5/1984 | Bekey et al. | 433/37 |
| 4,867,680 | 9/1989 | Hare et al. | 433/37 |
| 5,026,278 | 6/1991 | Oxman et al. | 433/41 |
| 5,040,976 | 8/1991 | Ubel, III et al. | 433/41 |
| 5,108,286 | 4/1992 | Freedman et al. | 433/37 |
| 5,415,544 | 5/1995 | Oxman et al. | 433/214 |
| 5,418,262 | 5/1995 | Göbel | 523/116 |
| 5,478,235 | 12/1995 | Schuldt et al. | 433/37 |
| 5,554,024 | 9/1996 | Ueda | 433/37 |

FOREIGN PATENT DOCUMENTS 6603639  3/1969  Germany.

OTHER PUBLICATIONS

3M Unitek Orthodontic Product Catalog, p.8–1, copyright 1996.

*Primary Examiner*—Nicholas D. Lucchesi
*Attorney, Agent, or Firm*—James D. Christoff

[57] ABSTRACT

A dental impression tray has a receptacle for receiving a quantity of dental impression material, and the receptacle is coated with an adhesive for enhancing the bond between the impression material and the tray. The adhesive is applied to the tray body at least sixteen hours before the impression material is placed in the receptacle. Advance coating of the adhesive onto the tray body provides a higher bond strength between the impression material and the tray than would otherwise be observed. Precoating of the tray by the manufacturer represents a time savings for the dental practitioner and also reduces the amount of volatilized solvent emitted from the adhesive that might otherwise be emitted in the dental office.

14 Claims, 2 Drawing Sheets

DENTAL IMPRESSION TRAY WITH IMPROVED ADHESION TO IMPRESSION MATERIAL

BACKGROUND OF THE INVENTION

1. Field of the Invention

This invention relates to a dental impression tray and a method of making a dental impression tray. The tray is characterized as having improved adhesion to impression material that is placed on the tray to make an impression of selected areas of a patient's oral cavity.

2. Description of the Related Art

Dental impression trays are often used by dentists, orthodontists, prosthodontists and others engaged in various fields of dentistry for obtaining a model or replica of selected areas of a patient's oral cavity. For example, a dentist or prosthodontist may desire to have a model of an area of a patient's oral cavity where one or more teeth are missing or damaged, so that suitable replacement teeth may be made in the lab using the model as a guide. In practice, the replacement teeth may be fitted by trial and error on the model and adjusted in size and shape as needed until a satisfactory size and shape are attained.

As another example, orthodontists often use models of a patient's teeth to study malformations of the teeth and jaws and plan a course of treatment. In some instances, the orthodontist may use models to trial fit one or more orthodontic appliances that will be used in the oral cavity to move teeth to desired positions. In other instances, models may be used to pre-position a set of orthodontic brackets and associated archwires that are later affixed to the patient's actual dental arches by a technique known as indirect bonding. Models are also used by orthodontists as ell as other dental practitioners to serve as a permanent record of a patient's teeth before and after treatment, and in some instances at selected intervals during the treatment program.

The use of dental models provides significant advantages for both the dental practitioner and the patient. Models enable the dental practitioner to adjust the shape and size of replacement teeth and tooth restorations and to adjust the position of orthodontic appliances and the like in the practitioner's laboratory or in an outside laboratory as desired and during a time that is most convenient for the dentist or lab personnel. Moreover, such initial size, shape and position adjustments can be carried out without requiring the patient to wait in the dental chair. Once a satisfactory fitting of the replacement teeth, restoration or orthodontic appliances is obtained on the model, the practitioner can readily install the same in place in the patient's oral cavity with few or no additional adjustments in many instances.

To obtain a dental model, an impression of desired areas of the patient's oral cavity is first obtained. To prepare an impression, a quantity of curable dental impression material is placed in an impression tray, and the tray is then positioned in the patient's oral cavity such that the impression material fills and surrounds the selected area of interest of the oral cavity. Once the impression material has cured, the impression material along with the tray is removed from the oral cavity.

To make a dental model from the impression, a second curable material is poured or otherwise placed in the cured impression material. Once the second material has cured, the impression material is removed from the resulting model. When made properly, the model provides an accurate physical replica of selected areas of the patient's tooth structure as well as adjacent portions of the patient's gingiva.

A variety of dental impression trays are available to hold dental impression material as impressions are made. Some dental impression trays have an overall, generally "U"-shaped configuration in plan view that matches the overall, generally "U"-shaped configuration of the patient's upper or lower dental arch. Other impression trays have an overall, generally "J"-shaped configuration in plan view for making an impression of one quadrant of the patient's oral cavity (i.e., the right or left half of either the patient's upper dental arch or lower dental arch). Still other impression trays have a generally straight configuration in plan view and are particularly useful in instances where an impression of areas representing less than a complete quadrant is needed.

Typically, a certain area of the dental impression tray serves as a receptacle for receiving dental impression material. In many dental impression trays, the receptacle comprises a channel having a generally "U"-shaped configuration in views transverse to the longitudinal axis of the channel (i.e., in reference planes perpendicular to the occlusal or "bite" plane of the patient). Other dental impression trays simply have a flat or generally flat surface for receiving the impression material. Some dental impression trays such as the tray described in U.S. Pat. No. 4,445,854 have upwardly-facing receptacles and downwardly-facing receptacles so that impressions of the upper and lower dental arch can be simultaneously obtained.

Dental impression trays are commercially available in a variety of materials. Some impression trays are made of metal such as stainless steel or aluminum. Other impression trays are made of a rigid plastic material such as polyethylene or polypropylene, or made of polystyrene foam (such as "STYROFOAM" brand polystyrene foam from Dow Chemical Company). Examples of impression trays made of a thermoplastic material that is malleable at elevated temperatures are described in U.S. Pat. Nos. 5,040,976 and 5,026,278.

A variety of dental impression materials are also commercially available. Elastomeric impression materials are generally preferred because the flexibility of the elastomeric material when cured enables the material to be readily removed from the oral cavity even when undercut areas, recesses and the like are present in the tooth structure. However, non-elastomeric impression material (such as plaster of Paris) has also been used in the past to a limited extent.

Elastomeric dental impression materials are often considered to fall in one of five major classes: reversible hydrocolloids, irreversible hydrocolloids, polysulfides, silicones and polyethers, of which the last four are thermosetting. An example of an irreversible hydrocolloid impression material is "UNIJEL-II" brand alginate impression material from 3M Unitek Corporation. An example of a silicone dental impression material is "EXPRESS" brand impression material from 3M Company.

Often, a means is provided to securely connect the impression material to the impression tray so that the impression material does not inadvertently detach from the receptacle of the impression tray. For example, when removing an impression tray bearing a quantity of elastomeric impression material from the patient's oral cavity, a significant force must sometimes be exerted on the tray in order to cause the cured impression material to flexibly deform as needed to disconnect from undercut areas or recesses of certain tooth structure. In such instances, the impression material should remain securely connected to the impression tray so that both the material and the tray are removed as a single unit from the oral cavity.

Some impression trays have holes or perforations placed along the receptacle to provide a mechanical means for coupling the impression material to the tray. In other instances, an adhesive is used to chemically bind the impression material to the receptacle of the tray. An example of a tray adhesive used in connection with alginate impression material is "HOLD" brand tray adhesive from Teledyne Getz. Tray adhesives are particularly useful for alginate and other hydrocolloid impression material that have little, if any, adhesive qualities.

Tray adhesives are conventionally used by the dental practitioner by applying the adhesive to the receptacle of the tray that receives the impression material immediately before the impression is to be taken. The impression material is then placed in the receptacle and the impression is made in the manner described above.

Unfortunately, it has been reported in some instances that dental patients have experienced a burning sensation or irritation when impression trays bearing tray adhesives have been placed in the oral cavity. It is suspected that such a burning sensation or irritation may be due in some instances to one or more solvents that volatilize from the tray adhesive. It is also suspected that in other instances the burning sensation or irritation may be due to direct contact of the tray adhesive with the patient's gingiva, especially in areas where the tray adhesive has spilled or has otherwise inadvertently contacted an outer surface of the tray that is typically not covered by the dental impression material. As can be appreciated, it would be desirable to reduce or eliminate such burning sensation or irritation if possible.

Furthermore, there is a continuing need in the art to improve impressioning procedures in the dental office, so that the time expended by the dental practitioner in carrying out the procedure and the time spent by the patient in the dental chair are reduced.

SUMMARY OF THE INVENTION

The present invention is directed in one aspect to a dental impression tray that includes a body having wall portions defining a receptacle for receiving a quantity of impression material. The tray includes an adhesive extending across at least some of the wall portions for enhancing the bond between the wall portions and the impression material. The adhesive extends across the wall portions for a period of at least sixteen hours prior to contact of the adhesive with impression material.

Another aspect of the present invention is directed to a dental impression tray assembly including an impression tray having wall portions defining a receptacle for receiving a quantity of impression material. The tray includes an adhesive extending across at least some of the wall portions for enhancing the bond between the wall portions and the impression material. The assembly includes a container receiving the tray, and the channel is devoid of impression material when the tray is received in the container.

The present invention also concerns a method of making a dental impression tray. The method comprises the steps of providing a dental impression tray body having wall portions defining a receptacle for receiving a quantity of impression material, and covering at least some of the wall portions with an adhesive to enhance the bond between the wall portions and the impression material. The method also includes the step of placing a quantity of impression material in the receptacle. The step of placing the quantity of impression material in the receptacle is carried out at least sixteen hours subsequent to the step of covering at least some of the wall portions with an adhesive.

It has been found that adhesion of the impression material to the tray body is enhanced when the adhesive has been placed on the tray at least twenty-four hours prior to contact with impression material. As a consequence, there is a significantly reduced risk that the cured impression material will inadvertently detach from the tray as the tray is removed from the oral cavity after the impression is taken. Advantageously, the adhesive can be pre-coated onto the impression tray by the manufacturer in automated fashion across precisely defined, preselected areas of the receptacle of the tray, such that the time that would otherwise be spent by the dental practitioner in carrying out this portion of the procedure is eliminated. Additionally, precoating of the impression tray by the manufacturer reduces the risk that the patient will experience a burning sensation or irritation when an impression is taken.

DETAILED DESCRIPTION OF THE PREFERRED EMBODIMENTS

Figure 1:
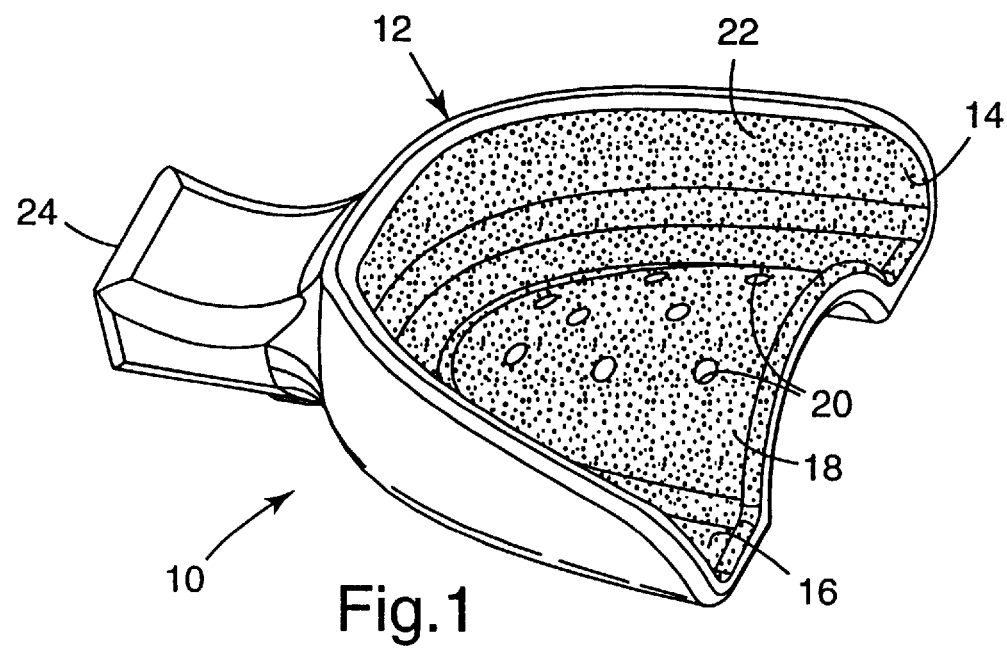
FIG. 1 is a top, front and left side perspective view of a dental impression tray constructed in accordance with one embodiment of the present invention.
Figure 2:
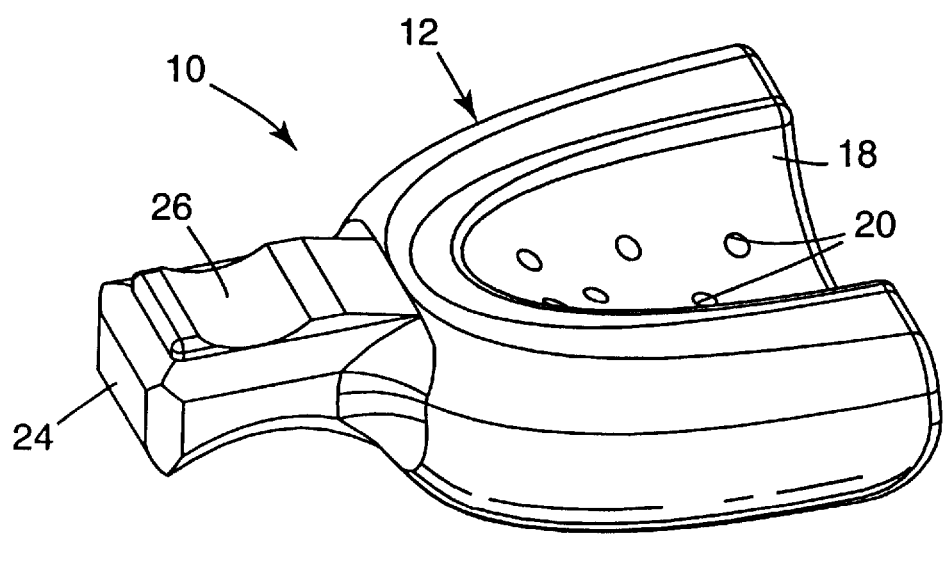
FIG. 2 is a bottom, rear and right side perspective view of the dental impression tray shown in FIG. 1.
Figure 3:
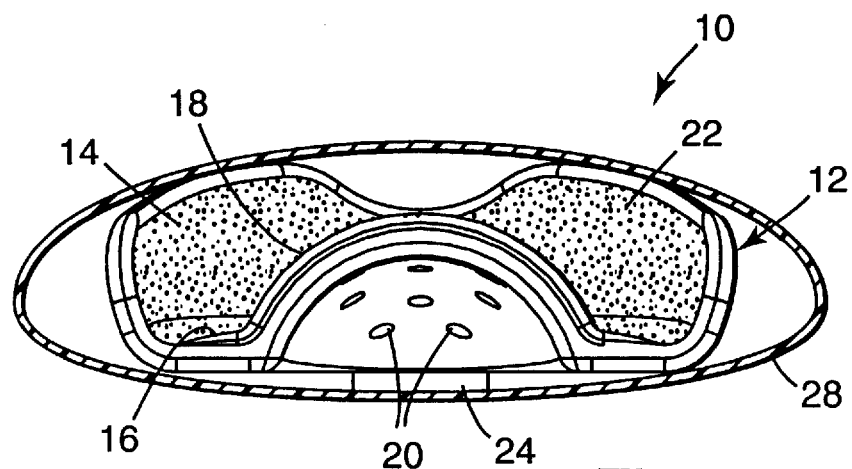
FIG. 3 is a front elevational view of the tray shown in FIGS. 1–2 along with a container for receiving the impression tray.

A dental impression tray constructed in accordance with one embodiment of the present invention is shown in FIGS. 1–3 and is designated broadly by the numeral 10. The impression tray 10 includes a body 12 having wall portions that define a receptacle 14. In the embodiment illustrated, the receptacle 14 includes a channel 16 as well as a convex central support 18 that is especially useful for taking an impression of an upper dental arch. (The central support 18 is eliminated for trays that are intended to take an impression of a lower dental arch.)

When viewed from the top of the tray 10, the channel 16 has a generally U-shaped configuration that matches the overall, generally U-shaped configuration of the patient's upper dental arch. The channel 16 also has a generally U-shaped configuration in vertical reference planes, as can be appreciated by the view of the front of the tray 10 that is shown in FIG. 3. The wall portions of the tray 10 that define the support 18 are connected to wall portions of the tray 10 that define an inner edge of the channel 16 such that the receptacle 14 represents a single, continuous recess.

The support 18 provides a space for the patient's tongue when an impression is taken. The support 18 also holds the impression material against the patient's palate when the impression is taken. Optionally, and as shown in the drawings, the support 18 is provided with a series of holes 20 that provide a mechanical interlock between the tray 10 and the impression material once the impression material has cured. Although not shown, the tray 10 may also be provided with other types of mechanical means for enhancing retention of the impression material in the tray 10 such as a series of grooves or ridges spaced along the various wall portions of the tray 10 that define the channel 16 and the support 18.

An adhesive 22 extends across at least some of the wall portions of the tray 10 that define the receptacle 14. Preferably, the adhesive 22 extends across essentially all of the wall portions of the channel 16 and the support 18 that define the receptacle 14. That is, when viewing FIGS. 1 and 3, the adhesive 22 is connected to the upwardly facing surfaces of the channel 16 and the support 18 as well as the inwardly facing surfaces on the upright side wall portions of the channel 16.

The tray 10 also includes a rear handle 24 to facilitate grasping the tray 10 and positioning the tray 10 in the patient's oral cavity. As shown in FIG. 2, the bottom of the handle 24 includes a recess 26. Although not shown in the drawings, the tray 10 may also include a rectangular recess that extends inwardly from the outer end of the handle 24.

Preferably, the tray 10 is integrally made of a synthetic resinous material such as polystyrene foam. Optionally, the tray 10 may be similar or identical to the polystyrene foam impression trays sold by 3M Unitek Corporation, catalog nos. 436-630 to 436-639. Alternatively, the tray 10 may be made of other materials such as aluminum or a synthetic resinous material such as polypropylene or polyethylene.

The adhesive 22 may be any adhesive that is suitable for bonding or increasing the bond strength between the impression material and the wall portions of the body 12 that define the receptacle 14. As an example, if the dental impression material is an alginate impression material such as "UNIJEL-II" brand impression material from 3M Unitek Corporation, the adhesive 22 may be liquid "HOLD" adhesive from Teledyne Getz. Other adhesives may also be used, and may be especially preferred when other types of impression materials are employed.

Once the adhesive 22 is placed across the wall portions defining the receptacle 14, the tray 10 is placed in a suitable container such as the bag-like container 28 illustrated in FIG. 3. Suitable materials for the container 28 include polyethylene. Once the tray 10 is in the container 28, the container 28 is preferably closed by a heat-sealing operation or optionally by a zipper-type closure that forms part of the container 28.

Other types of containers are also possible. For example, suitable containers include dust-free boxes or cartons made of rigid paper, boxboard or plastic. Preferably, each tray 10 is received in a separate container 28, or the trays 10 are arranged in an array and kept separated from one another when a plurality of such trays 10 are received in a single container 28, so that the adhesive 22 of one tray 10 does not contact and bond to wall portions of another tray 10.

It has been found that the bond strength between the body 12 of the tray 10 and the impression material placed in the receptacle 14 is enhanced when the adhesive 22 is placed in the receptacle 14 at least sixteen hours and more preferably at least 48 hours prior to placement of dental impression material in the receptacle 14. As a consequence, there is less likelihood that the impression material will separate from the body 12 when the tray 10 is removed from the patient's oral cavity.

In addition, pre-coating the tray body 12 with the adhesive 22 by the manufacturer results in a savings of time for the dental practitioner. Automated placement of the adhesive 22 in the receptacle 14 can provide a uniform coating of the adhesive 22 to ensure optimum bonding of the impression material to the tray 10 without wastage of the adhesive 22.

Moreover, pre-coating the body 12 with the adhesive 22 by the manufacturer greatly reduces the amount of flammable (and perhaps toxic) solvent that might otherwise vaporize in the confines of the dental office. Advance pre-coating of the adhesive 22 on the body 12 also reduces the amount of solvent that might otherwise vaporize during the period of time that the body 12 of the tray 10 is placed in the patient's oral cavity. In addition, by eliminating erroneous placement of the adhesive 22 on surfaces of the body 12 that contact the patient's oral tissues, it is likely that fewer patients will report a burning sensation or irritation as a result of the adhesive 22 when the body 12 is placed in the oral cavity.

The adhesive 22 may be applied to the body 12 in any suitable manner. For example, the adhesive 22 may be sprayed toward the receptacle 14 in automated, assembly-line fashion while remaining wall portions of the tray 10 are masked or otherwise blocked from the spray. Other methods of adhesive application (such as brushing or dipping) are of course possible.

EXAMPLE

Samples of tray body materials were prepared from polystyrene foam, aluminum and polyethylene. The polystyrene foam samples measured approximately 1.5×1.5×1.5 inch (3.7×3.7×3.7 cm). The aluminum samples measured approximately 1.5×1.5×0.1 inch (3.7×3.7×0.3 cm). The polyethylene samples were discs that measured approximately 3 inch (7.5 cm) in diameter and 0.03 inch (0.75 mm) thick.

Figure 4:
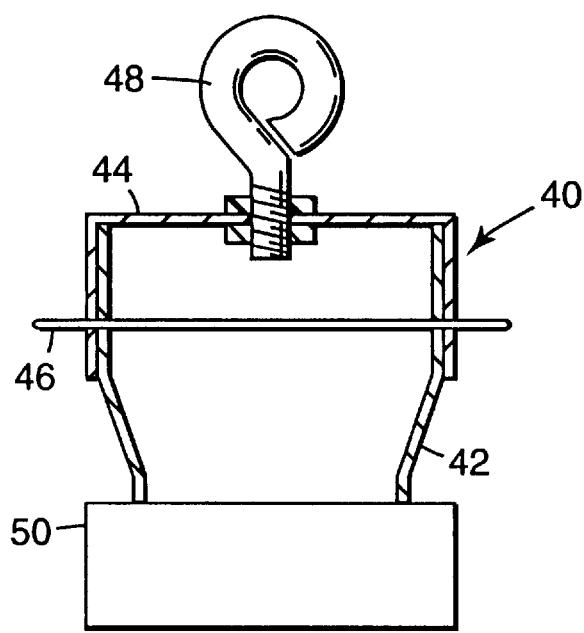
FIG. 4 is a side cross-sectional view of a fixture used for evaluating the adhesive bond between impression material and specimens representing trays of the invention.

A fixture 40 as shown in FIG. 4 was made by preparing a stainless steel housing 42 having a somewhat truncated conical shape central section and a stainless steel cover 44. A pin 46 extended through aligned apertures in the housing 42 and the cover 44 to releasably connect the cover 44 to the housing 42. An eyebolt 48 was secured by a pair of nuts to the center of the cover 44. The housing 42 had a lower circular opening.

For each experiment, a quantity of impression material was placed in the cavity of the fixture 40 and allowed to cure while in contact with the sample held against the lower opening of the fixture 40. The sample is designated by the numeral 50 in FIG. 4. Identification of the various impression materials used in the experiments is set out after the Table that follows.

In one set of experiments, the tray body samples were not coated with a tray adhesive. In a second set of experiments, the samples were coated with a tray adhesive and then applied within fifteen minutes against the lower opening of the fixture 40 while in contact with impression material within the housing 42. The second set of experiments are denoted by the term "Fresh" in the Table. Identification of the various tray adhesives used in the experiments is set out below the following Table.

A third set of experiments was carried out by coating polystyrene foam, aluminum and polyethylene samples with the tray adhesives. Those samples were then set aside for a minimum of sixteen hours, after which each sample was applied against the lower opening of the housing 42 and in contact with impression material within the housing. The third set of experiments are denoted by the term "Aged" in the Table.

In each experiment, the impression material was allowed to cure for approximately five minutes while in contact with the coated or uncoated samples. In each experiment, the sample and the fixture 40 were mounted on an "INSTRON" brand universal testing machine and the adhesive forces between the eyebolt 48 and the sample were measured using a crosshead speed of 0.05 inch/min. (1.3 mm/min.). The force necessary to detach the sample from the fixture 40 was then recorded. The experiments were repeated and the results were averaged.

The results of the adhesive testing are set out below:

TABLE

| Impression Material | Test Sample | Adhesive | Average Bond Strength (PSI) | Standard Deviation |
|---|---|---|---|---|
| Alginate | Polystyrene foam | None | 0.0 | 0.00 |
| Alginate | Polystyrene foam | Hold-Fresh | 1.32 | 0.34 |
| Alginate | Polystyrene foam | Hold-Aged | 2.00 | 0.48 |
| Alginate | Polystyrene foam | Red-Fresh | 2.07 | 0.80 |
| Alginate | Polystyrene foam | Red-Aged | 2.71 | 0.44 |
| Alginate | Polystyrene foam | Purple-Fresh | 2.16 | 0.53 |
| Alginate | Polystyrene foam | Purple-Aged | 3.07 | 0.44 |
| Alginate | Aluminum | None | 4.40 | 2.57 |
| Alginate | Aluminum | Purple-Fresh | 2.30 | 0.75 |
| Alginate | Aluminum | Purple-Aged | 4.66 | 1.41 |
| Alginate | Polyethylene | None | 0.13 | 0.04 |
| Alginate | Polyethylene | Hold-Fresh | 1.05 | 0.34 |
| Alginate | Polyethylene | Hold-Aged | 1.24 | 0.10 |
| Reversible Hydrocolloid | Polystyrene foam | None | 0.0 | 0.00 |
| Reversible Hydrocolloid | Polystyrene foam | Purple-Fresh | 0.71 | 0.40 |
| Reversible Hydrocolloid | Polystyrene foam | Purple-Aged | 1.07 | 0.51 |
| Reversible Hydrocolloid | Aluminum | None | 0.43 | 0.24 |
| Reversible Hydrocolloid | Aluminum | Purple-Fresh | 1.15 | 0.18 |
| Reversible Hydrocolloid | Aluminum | Purple-Aged | 3.69 | 1.82 |
| Reversible Hydrocolloid | Polyethylene | None | 0.09 | 0.09 |
| Reversible Hydrocolloid | Polyethylene | Hold-Fresh | 0.51 | 0.01 |
| Reversible Hydrocolloid | Polyethylene | Hold-Aged | 0.48 | 0.14 |
| Silicone "A" | Polystyrene foam | None | 11.66 | 0.31 |
| Silicone "A" | Polystyrene foam | 3M tray adhesive-Fresh | 20.33 | 5.23 |
| Silicone "A" | Polystyrene foam | 3M tray adhesive-Aged | 19.74 | 6.73 |
| Silicone "B" | Aluminum | None | 17.43 | 4.39 |
| Silicone "B" | Aluminum | 3M tray adhesive-Fresh | 28.64 | 7.53 |
| Silicone "B" | Aluminum | 3M tray adhesive-Aged | 27.24 | 7.97 |
| Silicone "C" | Polyethylene | None | 1.22 | 0.70 |
| Silicone "C" | Polyethylene | 3M tray adhesive-Fresh | 9.73 | 3.42 |
| Silicone "C" | Polyethylene | 3M tray adhesive-Aged | 10.30 | 2.73 |

Impression Materials

Alginate Impression Material - UNIJEL™ II Impression Material (from 3M Unitek Corporation) Unflavored (3M Unitek Catalog no. 710-043, Lot 5A1)

Reversible Hydrocolloid - COHERE™ Bonding Hydrocolloid (from Gingi-Pak) (Catalog no. 60500, Lot 1122954)

Silicone Impression Materials - 3M Express™ Polyvinylsiloxane (from 3M Company):

Silicone "A": Light Body - Regular Set (3M Catalog no. 7302H, Lot 6BR6V1)

Silicone "B": Light Body - Fast Set (3M Catalog no. 7301H, Lot 19960327)

Silicone "C": Regular Body (3M Catalog no. 7322H, Lot 6CT1W1)

Tray Adhesives

HOLD™ brand Tray Adhesive (from Teledyne Getz, Catalog no. 11462 Lot 30288)

"Red" Experimental - VERSAMID™ 100IT60 (2 parts) (from Henkel Corp.) diluted with isopropyl alcohol (1 part) and D&C Red # 7

"Purple" Experimental - VERSAMID™ 100IT60 (11 parts) diluted with isopropyl alcohol (9 parts) and D&C Violet # 2

3M Tray Adhesive (from 3M Company, Catalog no. 7307, Lot 6K)

The data show that the adhesive bond between the alginate impression material and the polystyrene foam samples was significantly enhanced when the tray adhesive was coated on the samples and allowed to age for at least sixteen hours before contact with the impression material. The polystyrene samples having aged adhesive demonstrated higher bond strengths regardless of whether the "HOLD", the "red" or the "purple" tray adhesive was used.

The uncoated aluminum samples adhered to alginate impression material. The adhesion was less when "fresh" tray adhesive was placed in contact with the alginate impression material, and was slightly greater when "aged" tray adhesive was placed in contact with the impression material.

Alginate impression material showed no significant adhesion to uncoated polyethylene samples. Moderate adhesion was observed for both the "fresh" and "aged" samples.

The reversible hydrocolloid impression material demonstrated little, if any, adhesion to the uncoated polystyrene, aluminum and polyethylene samples. Polystyrene samples bearing the "aged" adhesive demonstrated only a small increase in bond strength to the reversible hydrocolloid impression material in comparison to samples with the "fresh" tray adhesive. Aluminum samples bearing the "aged" tray adhesive showed a significant improvement in bond strength to reversible hydrocolloid materials in comparison to aluminum samples with the "fresh" tray adhesive. The polyethylene samples with the "aged" adhesive showed no improvement in adhesion to reversible hydrocolloid impression material in comparison to polyethylene samples with the "fresh" tray adhesive.

The silicone impression materials demonstrated adhesion to polystyrene, aluminum and polyethylene samples even in the absence of a tray adhesive. No significant improvement was noted by the samples bearing the "aged" adhesive in comparison to the samples bearing the "fresh" adhesive.

We claim:

1. A dental impression tray assembly including an impression tray having wall portions defining a receptacle for receiving a quantity of impression material, said tray including an adhesive extending across at least some of said wall portions for enhancing the bond between said wall portions and the impression material, said assembly including a container receiving said tray, said channel being devoid of impression material when said tray is received in said container, and wherein at least a majority of said adhesive is uncovered and spaced from said container.

2. The dental impression tray of claims 1, wherein said body is made of polystyrene foam.

3. The dental impression tray of claims 1, wherein said receptacle includes a generally U-shaped channel.

4. The dental impression tray of claim 1, wherein said adhesive extends across substantially the entire extent of said receptacle.

5. The dental impression tray of claim 1, wherein said body includes holes for providing mechanical retention to the impression material.

6. A method of making a dental impression tray comprising the steps of:
   providing a dental impression tray body having wall portions defining a receptacle for receiving a quantity of impression material;
   covering at least some of the wall portions with a liquid adhesive to enhance the bond between the wall portions and the impression material;

aging at least a majority of the adhesive by exposing the adhesive without contacting a cover; and placing a quantity of impression material in the receptacle, wherein said step of placing a quantity of impression material in the receptacle is carried out at least sixteen hours subsequent to said step of aging at least a majority of the adhesive.

7. The method of claim 6, wherein said step of providing a dental impression tray body includes the step of providing a tray body made of polystyrene foam.

8. The method of claim 6, wherein said step of placing a quantity of impression material in the receptacle includes the step of placing a quantity of alginate impression material in the receptacle.

9. The method of claim 6, and including the step of surrounding the dental impression tray body with a container subsequent to said step of covering at least some of the wall portions with an adhesive and prior to said step of placing a quantity of impression material in the receptacle.

10. A dental impression tray made by the method of claim 9.

11. The method of claim 6, wherein said step of placing a quantity of impression material in the receptacle is carried out at least 48 hours subsequent to said step of covering at least some of the wall portions with an adhesive.

12. A dental impression tray made by the method of claim 6.

13. A method of making a dental impression tray comprising the steps of:

providing a dental impression tray body having wall portions defining a receptacle for receiving a quantity of impression material;

coating at least some of the wall portions with a liquid adhesive to enhance the bond between wall portions and the impression material; and aging at least a majority of the adhesive by exposing the adhesive without contacting a cover at least sixteen hours prior to placing impression material in the receptacle.

14. A dental impression tray made by the method of claim 13.

* * * * *